United States Patent [19]

Kamashita et al.

[11] Patent Number: 5,374,765

[45] Date of Patent: Dec. 20, 1994

[54] METHOD FOR EXTRACTING AN AMINO ACID ESTER FROM A HYDROUS SOLUTION OF A MINERAL ACID SALT THEREOF

[75] Inventors: Tomoko Kamashita; Hiroyuki Yamashita; Teruyuki Nagata, all of Ohmuta; Masanobu Ajioka, Yokohama, all of Japan

[73] Assignee: Mitsui Toatsu Chemicals, Incorporated, Tokyo, Japan

[21] Appl. No.: 15,931

[22] Filed: Jan. 19, 1993

Related U.S. Application Data

[63] Continuation-in-part of Ser. No. 751,829, Aug. 30, 1991, abandoned.

[30] Foreign Application Priority Data

Sep. 3, 1990 [JP] Japan ................................. 2-230643

[51] Int. Cl.$^5$ ........................................... C07C 709/00
[52] U.S. Cl. ....................................... 560/40; 560/39; 560/153; 560/169; 560/171; 562/38
[58] Field of Search ...................... 562/38; 560/40, 39, 560/153, 169, 171

[56] References Cited

U.S. PATENT DOCUMENTS

| | | | |
|---|---|---|---|
| 3,988,341 | 10/1976 | Saari et al. | 260/326.14 |
| 4,680,403 | 7/1987 | Hisamiatsu et al. | 546/247 |

FOREIGN PATENT DOCUMENTS

| | | | |
|---|---|---|---|
| 267600 | of 1986 | Japan | 562/38 |
| 1210520 | 10/1970 | United Kingdom . | |

OTHER PUBLICATIONS

Vidaluc et al. "Optimization of the enzymatic synthesis of amino and esters" *Tetrahedron* vol. 39(2), pp. 269–274, 1983.

*Primary Examiner*—Marianne M. Cintins
*Assistant Examiner*—Keith MacMillan
*Attorney, Agent, or Firm*—Millen, White, Zelano & Branigan

[57] ABSTRACT

Disclosed is a method for extracting an amino acid ester from a hydrous solution which comprises adding thereto a water-insoluble organic solvent and then an amount of a base effective to liberate only a portion of the amino acid ester in free base form, and transferring the thus liberated amino acid ester in the free base form into the organic layer, and repeating the neutralization-extraction steps until all of the amino acid ester has been extracted.

13 Claims, No Drawings

METHOD FOR EXTRACTING AN AMINO ACID ESTER FROM A HYDROUS SOLUTION OF A MINERAL ACID SALT THEREOF

CROSS-REFERENCE TO RELATED APPLICATION

This application is a continuation-in-part application of Ser. No. 07/751,829, now abandoned, filed Aug. 30, 1991, whose disclosure is incorporated by reference herein.

BACKGROUND OF THE INVENTION

The present invention relates to a method for efficiently extracting an amino acid ester in free base form from a hydrous solution containing a mineral acid salt thereof.

Amino acid esters are important as an intermediate used in peptide synthesis. Methyl L-phenylalaninate, in particular, have recently drawn attention as a main raw material for Aspartame, an artificial sweetening.

For the esterification of an amino acid, ordinarily hydrogen chloride gas or concentrated sulfuric acid is introduced into an alcohol suspension of the amino acid.

The thus-produced amino acid ester is typically isolated in the form of a salt, such as the hydrochloride or the sulfate. When it is desired to use the amino acid ester as a reactant, e.g., in peptide synthesis, the salt is made into an aqueous solution, a base is added to the aqueous solution to convert the amino acid ester to its free base form, which is then extracted with an organic solvent, and the resulting organic solvent solution of the free base form is used per se in peptide synthesis. The reason for this is that amino acid esters tend to cause self-condensation to form a polypeptide or a diketo-piperazine derivative and accordingly have a problem in stability while their mineral acid salts have excellent storage stability.

When a free amino acid ester is needed, the above practice of isolating it in the form of a mineral acid salt is not advantageous from the viewpoints of the yield and operation.

Japanese Patent Publication No. 267600/1986 discloses a process for extracting free L-phenylalanine methyl ester with a water-immiscible organic solvent, after L-phenylalanine has been esterified with methanol in the presence of a strong acid as a catalyst followed by neutralizing the strong acid catalyst with base. Page 2, right lower column, lines 2–5 of that reference states that it is sufficient to use a molar amount of the base which is equal to or greater than the acid (such as sulfuric acid or hydrochloric acid) used as the catalyst. In general, a molar amount equal to or up to twice that of the strong acid is used, since an excessive base would hydrolyze the methyl ester. No specific pH value is disclosed for the neutralization procedure. However, the neutralization procedure of the reference is used to eliminate the strong acid used as the catalyst. It is not used to arrive at a neutral reaction solution.

Thus, after the neutralization procedure, the acid used as the catalyst is completely neutralized and, at the same time, the L-phenylalanine methyl ester in the solution is converted completely to its free base.

Because L-phenylalanine methyl ester is itself a base, after the neutralization of the strong acid, the solution will have a pH value much higher than the neutral value of pH 7, even if an amount of base in excess over the amount of the corresponding strong acid is not used.

In both of the above cases of (1) isolating a mineral acid salt of an amino acid ester, neutralizing the salt in its aqueous solution and extracting an amino acid ester and (2) esterifying an amino acid in the presence of an acid and subjecting the reaction mixture to neutralization and extraction to obtain an organic solvent solution containing an amino acid ester, there is a problem of hydrolysis of amino acid ester during neutralization and extraction. Heretofore, no adequate solution to this problem has existed.

The primary object of this invention is to provide an improved method for extracting an amino acid ester in free base form from a hydrous solution of a mineral acid salt of the amino acid ester.

Upon further study of the specification and appended claims, further objects and advantages of this invention will become apparent to those skilled in the art.

SUMMARY OF THE INVENTION

The above primary object is achieved by a method which maintains the pH of the aqueous layer phase at 7–8 during the extraction.

The above object is preferably achieved by carrying out the extraction a plurality of times, each time keeping the pH of the aqueous layer at 7–8 in each extraction.

The present invention makes possible the solvent extraction of an amino acid ester in free base form from an hydrous solution containing a mineral acid salt thereof in a manner which minimizes the reduction in yield caused by hydrolysis of the amino acid ester and to obtain the amino acid ester efficiently in the form of an organic solvent solution thereof.

DETAILED DESCRIPTION OF THE INVENTION

In order to minimize the hydrolysis of the amino acid ester in the step for preparing an organic solvent solution containing the amino acid ester from a hydrous solution containing a mineral acid salt of the amino acid ester, it is necessary to (1) add a water-insoluble organic solvent to the hydrous solution containing a mineral acid salt of the amino acid ester, then (2) add a base thereto to effect neutralization only to pH 7–8, thereby liberating only a portion of the amino acid ester, and (3) quickly transferring the liberated amino acid ester in free base form into the organic layer to minimize the time of contact of the free base form of amino acid ester with the aqueous phase.

The present inventors studied the rate of hydrolysis of amino acid esters in water. As a result, it was found that the pH of aqueous layer is the most important factor for the hydrolysis rate and that (1) when the pH is higher than 8, the hydrolysis of amino acid ester occurs quickly, but, when the pH is 8 or lower, sufficient stability for the hydrolysis is secured in the industrial production of amino acid ester and (2) the extraction efficiency by water-insoluble organic solvent is lower in terms of distribution ratio when the pH is lower and no practical extraction is obtained when the pH is lower than 7.

The above finding has led to the completion of a method which can minimize the hydrolysis of amino acid ester and which enables the efficient extraction of amino acid ester.

The present invention resides in a method for extracting an amino acid ester, which method comprises adding a water-insoluble organic solvent to a hydrous solution containing a mineral acid salt of an amino acid ester, then adding a base thereto to liberate an amino acid ester, and transferring the amino acid ester into the organic layer, which method is characterized in that the extraction is carried out by keeping the pH of the aqueous layer at 7-8.

The present invention also resides in a method for extracting an amino acid ester, which method comprises adding a water-insoluble organic solvent to a hydrous solution containing a mineral acid salt of an amino acid ester, then adding a base thereto to liberate the amino acid ester, and transferring the amino acid ester into the organic layer, which method is characterized in that the extraction is carried out a plurality of times by keeping the pH of the aqueous layer at 7-8 in each extraction.

When the extraction of an amino acid ester from its aqueous layer is carried out a plurality of times in order to obtain a higher extraction efficiency, if the pH adjustment to 7-8 is made only at the first extraction and no pH adjustment by the addition of a base is made at the second and later extractions, the pH of the aqueous layer gets gradually lower and the extraction efficiency decreases as the times of extraction increase. The reason is presumed as follows: that is, at pH 7-8, the mineral acid salt of an amino acid ester is not completely decomposed into the amino acid ester and there exist, in the aqueous layer, said mineral acid salt (which is acidic) and an amino acid ester (which is basic) liberated from said salt; at the subsequent extraction(s), the amino acid ester is transferred into the organic layer and the mineral acid salt remains in the aqueous layer, whereby the aqueous layer gets acidic and the pH gets lower.

The amino acid ester used in the present invention may be a racemic modification or an optical active substance. Its examples include alkyl or aromatic (e.g. methyl, ethyl, phenyl, benzyl) esters of neutral α-amino acids (e.g. glycine, alanine, valine, leucine, isoleucine, phenylalanine, serine, threonine), basic α-amino acids (e.g. lysine, alginine), acidic α-amino acids (e.g. aspartic acid, glutamic acid), β-phenylalanine, β-aminopropionic acid, γ-aminobutyric acid and aminobenzoic acid.

The mineral acid in the mineral acid salt of an amino acid ester used in the present invention is hydrochloric acid, sulfuric acid, nitric acid or phosphoric acid.

In the present invention, the hydrous solution containing a mineral acid salt of an amino acid ester includes not only an aqueous solution of said mineral acid salt but also a solution obtained by esterifying an amino acid in an alcohol in the presence of a mineral acid and adding water to the reaction mixture. In the hydrous solution, it is not necessary that the mineral acid salt of an amino acid ester be completely dissolved therein. The water in the solution obtained by adding water to the reaction mixture, may be a water after the addition of a water-insoluble organic solvent or a water added in the form of an aqueous base solution. The amount of water added is preferably about 5-50 times the weight of the mineral acid to be neutralized. When the amount of water is small, the inorganic salt generated by an acid-base reaction is precipitated, making difficult the separation operation. When the amount of water is large, the proportion of the amino acid ester distributed into the aqueous layer is large, reducing the extraction efficiency and the volume efficiency.

The water-insoluble organic solvent used as an extraction solvent in the present invention, can be any as long as it can be separated from the aqueous layer containing the inorganic salt generated by an acid-base reaction. As such a solvent, there can be mentioned, for example, hydrocarbons such as benzene, toluene, hexane and cyclohexane; halogenated hydrocarbons such as dichloromethane, chloroform, carbon tetrachloride, 1,2-dichloroethane and chlorobenzene; ethers such as ethyl ether, butyl ether, tetrahydrofuran and dioxane; and esters such as ethyl acetate, butyl acetate and methyl propionate. A halogenated hydrocarbon or an ester is preferable because of the higher extraction efficiency.

The amount of water-insoluble organic solvent used in one extraction operation is preferably about 0.1-10 times the weight of the hydrous solution containing a mineral acid salt of an amino acid ester. While the percent extraction is higher as the amount of water-insoluble organic solvent used is larger, the use of the solvent in an amount larger than 10 times is disadvantageous industrially in view of the concentration of amino acid ester in extract, the volume efficiency and the solvent recovery. The use of the solvent in an amount smaller than 0.1 time makes large the amount of amino acid ester remaining in the aqueous layer, making it necessary to increase the times of extraction.

The base used in the present invention includes inorganic bases typified by alkali metal hydroxides such as sodium hydroxide and potassium hydroxide, alkali metal hydrogencarbonates such as sodium hydrogencarbonate and potassium hydrogencarbonate, and alkali metal carbonates such as sodium carbonate and potassium carbonate, as well as organic bases typified by tertiary amines such as triethylamine and tributylamine. An inorganic base is preferable because it is not taken into the organic solvent layer containing an amino acid ester.

Preferably, the base is added as it is or in the form of an aqueous solution while the mixture of a hydrous solution containing a mineral acid salt of an amino acid ester with a water-insoluble organic solvent is being stirred. When a strong base, for example, an alkali metal hydroxide is used, it is preferably added dropwise in the form of a 20% or lower water solution in order to suppress the hydrolysis of amino acid ester caused by local pH increase.

With respect to the temperature employed during extraction, a lower temperature gives slower hydrolysis of amino acid ester. However, extraction can be preferably carried out at 0°-50° C. as long as the pH of the aqueous layer is kept at 7-8. A temperature lower than 0° C. is not practical because the aqueous solution may be solidified. A temperature higher than 50° C. is not preferable because the amino acid ester is hydrolyzed easily.

The pH of the aqueous layer during extraction is 7-8 as mentioned above. A pH higher than 8 gives a higher percent extraction but incurs sharp increase in hydrolysis of a amino acid ester. A pH lower than 7 causes no hydrolysis of amino acid ester, but reduces percent extraction significantly and is not practical.

The present invention is hereinafter described in detail by way of Examples. However, the present invention is not restricted to these Examples.

EXAMPLES 1-11 AND COMPARATIVE EXAMPLES 1-18

0.1 mole of a mineral acid salt of an amino acid ester, shown in Table 1 was dissolved or suspended in 30 g of water. Thereto was added 60 g of 1,2-dichloroethane.

While the mixture was kept at 20°-25° C. and stirred, a 20% water solution of sodium hydroxide was dropwise added thereto in 0.5 hour, and then stirring and extraction were carried out for 0.5 hour while the pH of the aqueous layer was kept at a constant level in the range of 6.5-8.5. The organic layer was separated from the aqueous layer. Then, there were measured percent extraction of fed amino acid ester in organic layer, percent remaining of said ester in aqueous layer, and percent hydrolysis of said ester in aqueous layer (the hydrolyzed ester remains in the aqueous layer as an amino acid). The results are shown in Table 1.

at 7.5. The organic layer was separated from the aqueous layer. The organic layer contained 29.4 g (percent extraction=85%) of methyl L-phenylalaninate, and the aqueous layer contained 4.8 g of methyl L-phenylalaninate and 1.6 g of L-phenylalanine. Therefore, the percent hydrolysis of methyl L-phenylalaninate during extraction was only 1.2%.

70 g of 1,2-dichloroethane was added to the aqueous layer. Thereto was dropwise added a 8% water solution of sodium hydroxide in 10 minutes with stirring. Successively, stirring and second extraction were carried out for 0.5 hour while the pH of the aqueous layer was

TABLE 1

|  | Mineral acid salt of amino acid ester | pH | Percent extraction of ester in organic layer (%) | Ester in aqueous layer | |
|---|---|---|---|---|---|
|  |  |  |  | Percent remaining (%) | Percent hydrolysis (%) |
| Comparative Example 1 | Methyl L-phenyl-alaninate hydrochloride | 6.5 | 91 | 9 | 0 |
| Example 1 |  | 7.0 | 96 | 4 | 0 |
| Example 2 |  | 7.5 | 97 | 3 | 0 |
| Example 3 |  | 8.0 | 97 | 2 | 1 |
| Comparative Example 2 |  | 8.5 | 96 | 1 | 3 |
| Comparative Example 3 | Ethyl L-phenyl-alaninate hydrochloride | 6.5 | 92 | 8 | 0 |
| Example 4 |  | 7.5 | 98 | 2 | 0 |
| Comparative Example 4 |  | 8.5 | 96 | 1 | 3 |
| Comparative Example 5 | Benzyl L-phenyl-alaninate hydrochloride | 6.5 | 94 | 6 | 0 |
| Example 5 |  | 7.5 | 99 | 1 | 0 |
| Comparative Example 6 |  | 8.5 | 97 | 1 |  |
| Comparative Example 7 | Phenyl L-phenyl-alaninate hydrochloride | 6.5 | 94 | 6 | 0 |
| Example 6 |  | 7.5 | 97 | 1 | 2 |
| Comparative Example 8 |  | 8.5 | 92 | 1 | 7 |
| Comparative Example 9 | Methyl L-serinate hydrochloride | 6.5 | 86 | 14 | 0 |
| Example 7 |  | 7.5 | 95 | 5 | 0 |
| Comparative Example 10 |  | 8.5 | 94 | 2 | 4 |
| Comparative Example 11 | Methyl L-lysinate hydrochloride | 6.5 | 82 | 18 | 0 |
| Example 8 |  | 7.5 | 91 | 9 | 0 |
| Comparative Example 12 |  | 8.5 | 94 | 3 | 3 |
| Comparative Example 13 | Methyl L-aspartate hydrochloride | 6.5 | 88 | 12 | 0 |
| Example 9 |  | 7.5 | 96 | 3 | 1 |
| Comparative Example 14 |  | 8.5 | 96 | 1 | 3 |
| Comparative Example 15 | Ethyl o-aminobenzoate hydrochloride | 6.5 | 94 | 6 | 0 |
| Example 10 |  | 7.5 | 97 | 2 | 1 |
| Comparative Example 16 |  | 8.5 | 96 | 1 | 3 |
| Comparative Example 17 | Methyl γ-aminobutyrate hydrochloride | 6.5 | 89 | 11 | 0 |
| Example 11 |  | 7.5 | 96 | 4 | 0 |
| Comparative Example 18 |  | 8.5 | 95 | 2 | 3 |

EXAMPLE 12

36 g of 98% sulfuric acid was added to a suspension of 33.1 g of L-phenylalanine in 60 g of methanol, and a reaction was carried out at 40°-50° C. for 7 hours. The reaction mixture contained 34.6 g of methyl L-phenylalaninate and 1.2 g of unreacted L-phenylalanine. Thereinto was fed 70 g of 1,2-dichloroethane, and about 220 g of a 8% water solution of sodium hydroxide was dropwise added in 1.5 hours with stirring at 20°-25° C. Successively, stirring and extraction were carried out for 0.5 hour while the pH of the aqueous layer was kept at 7.5. The organic layer was separated from the aqueous layer. The organic layer contained 4.0 g (percent extraction=83%) of methyl L-phenylalaninate, and the aqueous layer contained 0.75 g of methyl L-phenylalaninate and 1.65 g of L-phenylalanine.

The aqueous layer after the second extraction was subjected to the same procedure as in the second extraction, to carry out a third extraction. The organic layer contained 0.62 g (percent extraction=83%) of methyl L-phenylalaninate, and the aqueous layer contained 0.12 g of methyl L-phenylalaninate and 1.66 g of L-phenylalanine.

After the third extraction, the total organic layer contained 34.02 g (percent extraction=98%) of methyl L-phenylalaninate and the percent hydrolysis of methyl L-phenylalaninate was only 1.3%.

The results are shown in Table 2.

TABLE 2

| Order of extraction | L-PheOMe in organic layer (g) | Percent extraction (%) | In aqueous layer L-PheOMe (g) | L-Phe (g) | Percent hydrolysis (%) |
|---|---|---|---|---|---|
| Reaction mixture | — | — | 34.6 | 1.2 | — |
| 1st extraction | 29.4 | 85 | 4.8 | 1.6 | 1.2 |
| 2nd extraction | 4.0 | 83 | 0.75 | 1.65 | 1.0 |
| 3rd extraction | 0.62 | 83 | 0.12 | 1.66 | 1.3 |
| After total extraction | 34.02 | 98 | 0.12 | 1.6 | 1.3 |

Notes:
L-PheOMe = methyl L-phenylalaninate
L-Phe = L-phenylalanine

EXAMPLE 13

The same extraction procedure as in Example 12 was repeated except that the 1,2-dichloroethane used in Example 12 was changed to toluene. The results are shown in Table 3.

TABLE 3

| Order of extraction | L-PheOMe in organic layer (g) | Percent extraction (%) | In aqueous layer L-PheOMe (g) | L-Phe (g) | Percent hydrolysis (%) |
|---|---|---|---|---|---|
| Reaction mixture | — | — | 34.6 | 1.2 | — |
| 1st extraction | 20.2 | 59 | 14.0 | 1.6 | 1.2 |
| 2nd extraction | 8.1 | 58 | 5.75 | 1.75 | 1.1 |
| 3rd extraction | 3.3 | 58 | 2.38 | 1.82 | 1.2 |
| After total extraction | 31.6 | 91 | 2.38 | 1.82 | 1.8 |

Notes:
L-PheOMe = methyl L-phenylalaninate
L-Phe = L-phenylalanine

COMPARATIVE EXAMPLE 19

The same extraction procedure as in Example 12 was repeated except that the second and third extractions were carried out using no aqueous sodium hydroxide solution. The aqueous layer had pHs of 6.8 and 5.8 after the second and third extractions, respectively. Thus, the pH of the aqueous layer became lower after the second and third extractions. The results are shown in Table 4.

TABLE 4

| Order of extraction | L-PheOMe in organic layer (g) | Percent extraction (%) | In aqueous layer L-PheOMe (g) | L-Phe (g) | Percent hydrolysis (%) |
|---|---|---|---|---|---|
| Reaction mixture | — | — | 34.6 | 1.2 | — |
| 1st extraction | 29.4 | 85 | 4.8 | 1.6 | 1.2 |
| 2nd extraction | 2.1 | 44 | 2.7 | 1.6 | 0 |
| 3rd extraction | 0.7 | 26 | 2.0 | 1.6 | 0 |
| After total extraction | 32.2 | 93 | 2.0 | 1.6 | 1.2 |

Notes:
L-PheOMe = methyl L-phenylalaninate
L-Phe = L-phenylalanine

In Example 12 wherein the pH of the aqueous layer was kept at 7.5 in each extraction, the percent extraction was substantially constant (83–85%) in each extraction and, after the final extraction, 98% in total of methyl L-phenylalaninate could be extracted. Meanwhile, when the pH of the aqueous layer was not kept at 7.5 in the second and third extractions, the percent extraction decreased stepwise from 85% (first extraction) to 44% (second extraction) and 26% (third extraction), and only 93% in total of methyl L-phenylalaninate was extracted.

EXAMPLES 14–15 AND COMPARATIVE EXAMPLES 20–21

The first extraction procedure of Example 13 was repeated except that the pH of the aqueous layer was kept at 6.5, 7.0, 8.0 or 8.5. The results are shown in Table 5.

TABLE 5

| | pH of aqueous layer | L-PheOMe in organic layer (g) | Percent extraction (%) | In aqueous layer L-PheOMe (g) | L-Phe (g) | Percent hydrolysis (%) |
|---|---|---|---|---|---|---|
| Comparative Example 20 | 6.5 | 3.1 | 9 | 31.5 | 1.2 | 0 |
| Example 14 | 7.0 | 10.7 | 31 | 23.9 | 1.2 | 0 |
| Example 13 | 7.5 | 20.2 | 59 | 14.0 | 1.6 | 1 |
| Example 15 | 8.0 | 26.1 | 78 | 7.4 | 2.3 | 3 |
| Comparative Example 21 | 8.5 | 27.0 | 85 | 4.8 | 4.0 | 8 |

EXAMPLES 16–18

The first extraction procedure of Example 12 was repeated except that the extraction was carried out at various temperature ranges each of 0°–80° C., different from the range employed in Example 12. The results are shown in Table 6, together with those of Example 12.

TABLE 6

|  | Temperature (°C.) | L-PheOMe in organic layer (g) | Percent extraction (%) | In aqueous layer | | Percent hydrolysis (%) |
| --- | --- | --- | --- | --- | --- | --- |
|  |  |  |  | L-PheOMe (g) | L-Phe (g) |  |
| Example 16 | 0-5 | 27.9 | 81 | 6.6 | 1.3 | 0.3 |
| Example 12 | 20-25 | 29.4 | 85 | 4.8 | 1.6 | 1.2 |
| Example 17 | 45-50 | 29.6 | 88 | 4.0 | 2.2 | 2.9 |
| Example 18 | 75-80 | 29.3 | 90 | 3.2 | 3.3 | 6.1 |

EXAMPLES 19-21

The first extraction procedure of Example 12 was repeated except that the amount of 1,2-dichloroethane used was varied. The results are shown in Table 7, together with those of Example 12.

TABLE 7

|  | 1,2-Dichloroethane (g) | L-PheOMe in organic layer (g) | Percent extraction (%) | In aqueous layer | | Percent hydrolysis (%) |
| --- | --- | --- | --- | --- | --- | --- |
|  |  |  |  | L-PheOMe (g) | L-Phe (g) |  |
| Example 19 | 20 | 21.8 | 63 | 12.2 | 1.8 | 1.7 |
| Example 12 | 70 | 29.4 | 85 | 4.8 | 1.6 | 1.2 |
| Example 20 | 200 | 31.9 | 93 | 2.4 | 1.5 | 0.9 |
| Example 21 | 2000 | 32.9 | 96 | 1.4 | 1.5 | 0.9 |

EXAMPLES 22-25

The first extraction procedure of Example 12 was repeated except that the type of the water-insoluble solvent used was varied. The results are shown in Table 8.

TABLE 8

|  | Solvent | L-PheOMe in organic layer (g) | Percent extraction (%) | In aqueous layer | | Percent hydrolysis (%) |
| --- | --- | --- | --- | --- | --- | --- |
|  |  |  |  | L-PheOMe (g) | L-Phe (g) |  |
| Example 22 | Benzene | 21.1 | 61 | 13.1 | 1.5 | 0.9 |
| Example 23 | Dichloromethane | 28.0 | 81 | 6.2 | 1.6 | 1.2 |
| Example 24 | Butyl ether | 26.8 | 77 | 7.5 | 1.5 | 0.9 |
| Example 25 | Ethyl acetate | 30.1 | 87 | 4.3 | 1.4 | 0.6 |

The entire disclosures of all applications, patents and publications, cited above and below, and of corresponding application Japanese No. 230643/1990, filed Sep. 3, 1990, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for producing a hydrous solution of and extracting therefrom an amino acid ester selected from the group consisting of alkyl and aromatic esters of α-amino acids, of β-amino acids, of τ-amino acids and of amino benzoic acid, which method comprises the steps of producing the hydrous solution by esterifying an amino acid with an excess of a lower alkanol using a mineral and as esterification catalyst, adding a water-insoluble organic solvent to the thus-produced hydrous solution containing a mineral acid salt of the amino acid ester to form an aqueous phase and a solvent phase, then adding an amount of base thereto sufficient to bring the pH to 7-8 and thereby convert only a portion of the mineral acid salt of the amino acid ester to the free base form, and promptly extracting the free base form of the amino acid ester from the aqueous phase and transferring it into the organic phase while keeping the pH of the aqueous phase at 7-8.

2. A method according to claim 1, wherein the extraction is carried out a plurality of times, each time keeping the pH of the aqueous layer at 7-8 pH.

3. A method according to claim 1, wherein the hydrous solution is a water solution.

4. A method according to claim 1, wherein the hydrous solution is an aqueous methanol solution.

5. A method according to claim 1, wherein the amino acid ester is a methyl ester of L-phenylalaninate.

6. A method according to claim 1, wherein the base is an inorganic base.

7. A method according to claim 1, wherein the extraction is carried out at a temperature of 0°-50° C.

8. A method according to claim 2, wherein the amino acid ester is the methyl ester of methyl L-phenylalaninate; the hydrous solution is a water solution or an aqueous methanol solution; and the pH is maintained at 7-8 with strong base.

9. A method according to claim 8, wherein the base is an inorganic base and the extraction is carried out at a temperature of 0°-50° C.

10. A method according to claim 8, wherein the pH is maintained at 7-8 during the extractions by the addition of the base to the hydrous solution of the mineral acid salt at the second and any later extractions.

11. A method according to claim 1, wherein the base is a strong base which is added in a manner effective to suppress the hydrolysis of the amino acid ester by a localized increase in pH above 8.

12. A method according to claim 1, wherein the pH is brought to 7-8 with strong base and maintained thereat by adding the strong base thereto during each extraction in a manner effective to suppress the hydrolysis of the amino acid ester by a localized increase in pH above 8.

13. A method according to claim 12, wherein the hydrous solution is an aqueous methanol solution.

* * * * *